United States Patent [19]

Mitchiner et al.

[11] 4,015,606

[45] Apr. 5, 1977

[54] METHOD AND MEANS FOR CONTROLLING THE FREEZE ZONE OF A CRYOSURGICAL PROBE

[75] Inventors: Robert K. Mitchiner, Boulder, Colo.; Wayne A. Russell, Chelmsford, Mass.

[73] Assignee: Dynatech Corporation, Burlington, Mass.

[22] Filed: Sept. 9, 1975

[21] Appl. No.: 611,620

[52] U.S. Cl. .............................. 128/303.1; 62/293
[51] Int. Cl.$^2$ ........................................ A61B 17/36
[58] Field of Search ................... 62/293; 128/303.1

[56] References Cited

UNITED STATES PATENTS

| 3,502,081 | 3/1970 | Amoils | 128/303.1 |
| 3,782,386 | 1/1974 | Barger et al. | 128/303.1 |
| 3,910,277 | 10/1975 | Zimmer | 128/303.1 |
| 3,913,581 | 10/1975 | Ritson et al. | 128/303.1 |

Primary Examiner—Channing L. Pace
Attorney, Agent, or Firm—Cesari and McKenna

[57] ABSTRACT

A cryosurgical probe has a refrigerant supply conduit for conducting refrigerant to the hollow thermally-conductive probe tip. A refrigerant exhaust conduit extends through the probe into the tip and the end of the exhaust conduit in the tip is positioned a selected distance proximally of the end of the supply conduit. Thus, when refrigerant flows through the supply conduit to the tip, it tends to follow a flow path taking it more or less directly to the exhaust conduit. This creates a dead gas space inside the tip proximally of the end of the exhaust conduit, thereby minimizing direct cooling of portions of the probe adjacent to and proximally of the dead gas space and confining the freeze zone distal to that space. By adjusting the height of the exhaust conduit end proximally of the supply conduit end, the size of the freeze zone at the tip can be controlled. Further, if the probe has a defrost mode, defrost is enhanced because only the working end of the tip need be warmed.

5 Claims, 2 Drawing Figures

METHOD AND MEANS FOR CONTROLLING THE FREEZE ZONE OF A CRYOSURGICAL PROBE

BACKGROUND OF THE INVENTION

This invention relates to a cryosurgical probe. It relates more particularly to method and means for limiting and controlling the size of the freeze zone at the probe tip.

Cryosurgical probes are finding wider application in various types of surgical procedures such as correcting retinal detachments, removing cataracts, treating cervicitis, cervical erosion, cysts, etc. Basically, the probe comprises a handle with a hollow thermally-conductive tip protruding from the handle. A small diameter conduit extending through the handle to the probe tip conducts fluid refrigerant to the tip. As the refrigerant leaves the supply conduit, it cools by expansion, evaporation, and by the Joule-Thompson effect depending upon the type of refrigerant and its phase. The cooled refrigerant, in turn, cools the walls of the tip to a temperature low enough to freeze human tissue. The refrigerant exhausts from the tip through an exhaust conduit extending through the handle and leading ultimately to the atmosphere.

When used for cataract removal, for example, the probe tip is placed in contact with tissue, the tissue becomes frozen and adheres to the tip so that the tissue can be pulled away. Also, if the tip is held in contact with the tissue for a sufficient period of time, scar tissue forms to "weld" tissue together. The mending of a detached retina is accomplished this way.

Further, some probes includes provision for rapidly heating the probe tip electrically or by flowing warm fluid through the tip following a surgical procedure so that the tip can be released quickly from the tissue.

The probe tips assume a variety of sizes depending upon their purpose. Opthalmic probes, for example, have a straight or curved prove tip on the order of 0.070 inch in diameter and from ½ to 1 inch long. Other probes such as those used in gyneocological procedures have tips which are as large as 1 inch in diameter and several inches long. As a general rule, however, only the very tip end is used to freeze tissue during an operation. Unfortunately, with conventional probes, the entire tip freezes. In some cases, even metallic parts above the tip become cold. Unavoidably, then, portions of the probe other than the working end of the tip contact tissue not in the target area thereby freezing it and causing pain and possible injury to the patient.

One suggested solution to this problem has been to make the tips shorter so that they have less area to contact tissue. However, unless the tip projects an appreciable distance from the handle, it is very difficult to insert the tip end sufficiently and position it on the target tissue. Accordingly, prior probes still have this disadvantage.

SUMMARY OF THE INVENTION

Accordingly, it is an object of the present invention to provide a method of limiting and controlling the tip freeze zone of a cryosurgical probe.

Another object is to provide a cryosurgical probe which limits the portion of the probe tip that becomes cold enough to freeze tissue.

Yet another object of the invention is to provide a cryosurgical probe whose tip only becomes cold enough to freeze tissue at a selected zone at the working end of the tip.

A further object of the invention is to provide a cryosurgical probe whose tip freeze zone can be varied in size.

Other objects will in part be obvious and will in part appear hereinafter.

The invention accordingly comprises the series of steps and combination of elements and arrangement of parts which will be exemplified in the following detailed description and the scope of the invention will be indicated in the claims.

In general, the tip freeze zone of a cryosurgical probe having a supply conduit extending into the probe tip is controlled by extending the refrigerant exhaust conduit into the tip so that it terminates proximally of the end of the supply conduit. Fluid refrigerant entering the tip through the supply conduit cools in accordance with known phenomena thereby cooling the working end of the tip directly opposite the supply conduit.

The refrigerant fluid in the tip tends to flow more or less directly to the end of the exhaust conduit so that a dead gas space forms inside the tip in the region proximally of the end of the exhaust conduit. the stagnant gas in this space acts as an insulator so that portions of the probe proximally of the end of the exhaust conduit are isolated from, and not cooled directly by, the refrigerant fluid. Consequently, the walls of the tip and handle proximally of the end of the exhaust conduit do not become cold enough to freeze tissue. Thus even if those proximal portions of the probe inadvertantly contact tissue in the vicinity of the target area, they do not become adhered to such tissue. Rather the freeze zone is limited to the working end of the probe tip.

Further, in one probe embodiment, provision is made for adjusting the height of the exhaust conduit end proximally of the supply conduit end inside the probe tip so that the freeze zone can be made larger or smaller as needed for each given surgical procedure.

With this technique then, one can limit and control the amount of the probe tip that becomes sufficiently cold to freeze tissue. Accordingly it should give the doctor much better control over the size of the ice ball formed in tissue and decrease the chances of the probe tip adhering to or damaging healthy tissue adjacent the target area. Also, since only the working end of the probe becomes cold enough to freeze tissue, more heat is available to separate the working end of the probe from tissue during the defrost cycle.

Thus, since the present approach can be used to control the freeze zone at the tip of a cryosurgical probe which is cooled either by a liquid or gaseous refrigerant, it should find wide application in cryosurgery.

BRIEF DESCRIPTION OF THE DRAWING

For a fuller understanding of the nature and objects of the invention, reference should be had to the following detailed description taken in connection with the accompanying drawing in which.

DESCRIPTION OF THE PREFERRED EMBODIMENTS

Figure 1:
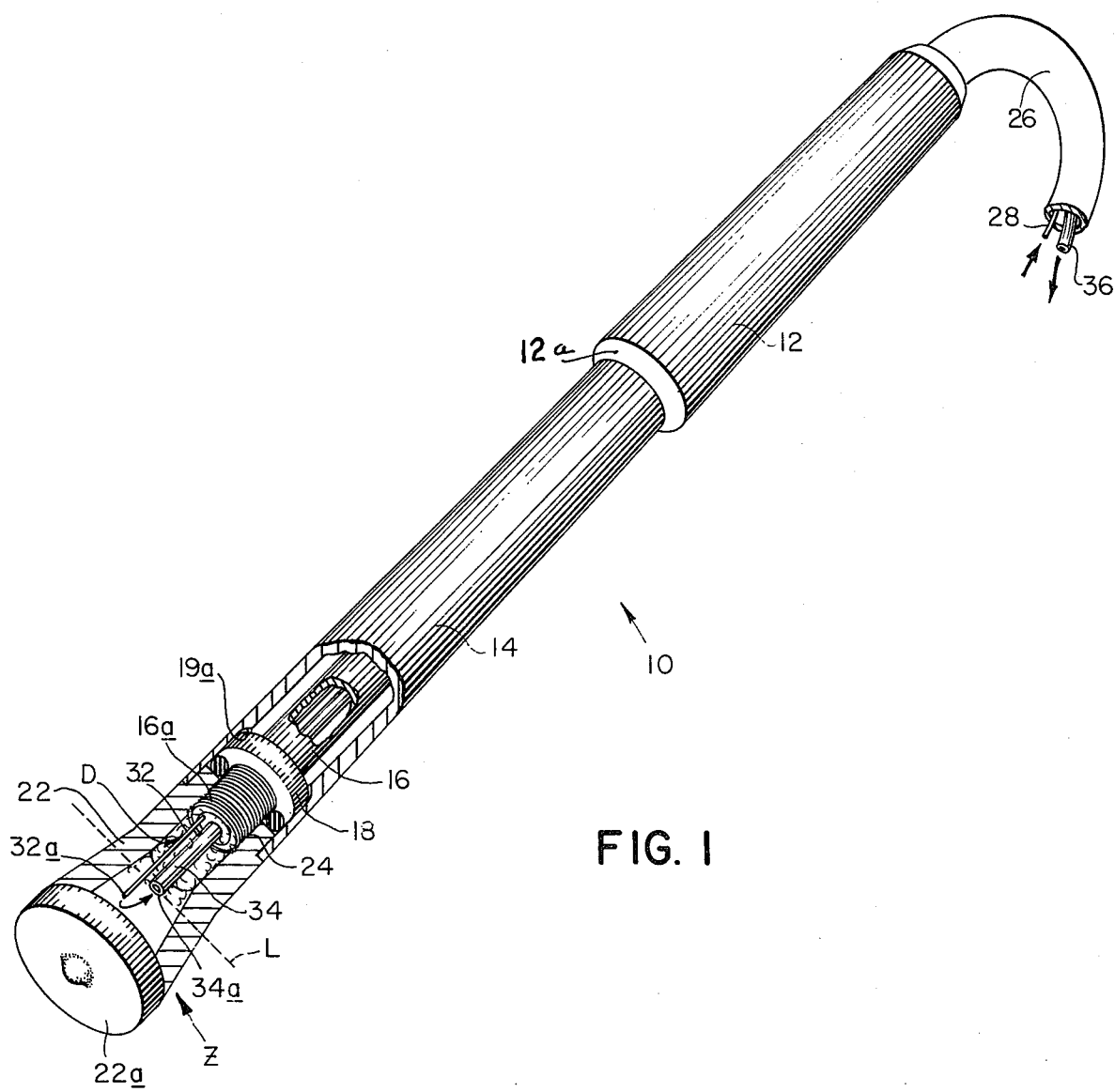
FIG. 1 is a perspective view with parts cut away showing a cryosurgical probe embodying the principles of this invention.

Referring now to FIG. 1 of the drawing, there is illustrated generally at 10 a relatively large cryosurgical probe of the type used to treat cervical eorsion, skin lesions and the like. This probe is cooled by a gaseous refrigerant such as carbon dioxide or nitrous oxide. However, it should be understood that the present technique applies equally well to probes having different configurations for the treatment of other disorders or which are cooled by conventional liquid refrigerants.

The probe 10 includes a generally cylindrical handle 12 made of a suitable impact-resistant, thermally insulating plastic. Projecting from the lowr end of the handle is a smaller diameter generally cylindrical shroud 14 made of a similar material. The handle 12 and shroud 14 house a long metal sleeve 16 having a circumferential flange 18 near its distal end. Flange 18 seats in a counterbore 19a at the distal end of shroud 14 and the portion of the sleeve beyond the flange is exteriorly threaded as indicated at 16a. A conventional probe tip 22 is screwed onto the threaded sleeve portion 16a as shown in that figure.

Tip 22 is hollow and made of a metal having a good thermal conductivity such as copper. The tip may be variously shaped depending upon the surgical problem that it is designed to treat. The illustrated tip is flared with a round, generally flat end 22a. However, it should be understood that the tip could be cylindrical with either a round, flat or pointed end and it may be curved so that it can reach the target area with minimum discomfort to the patient.

The proximal, smaller diameter end of tip 22 is interiorly threaded at 24 to receive the threaded sleeve portion 16a. Also, its outer diameter is preferably the same as that of shroud 14 so that when the tip is in place, its outside surface becomes essentially an extension of the outside surface of shroud 14.

Still referring to FIG. 1, a sheath 26 extends into the proximal end of handle 12, the handle being beveled at 12a where it joins the shroud 14. The sheath contains a flexible supply hose 28 which is connected inside the probe to the proximal end of a supply conduit 32 which extends down into tip 22. That conduit terminates at 32a just proximally of the tip end 22a. Fluid refrigerant is introduced into the probe tip 22 via conduit 32.

The refrigerant exhausts from the tip 22 through an exhaust conduit 34 whose end 34a is positioned in tip 22 proximally of the end of the supply conduit. Conduit 34 extends from the tip through sleeve 16. Inside the probe handle 12, the proximal end of the exhaust conduit is connected to a flexible exhaust hose 36 inside sheath 26 which leads ultimately to the atmosphere. When the probe 10 is operating in its freeze mode, refrigerant expelled from supply conduit end 32a cools to a very low temperature in accordance with the well known phenomena thereby cooling the probe tip end 22a.

In conventional probes the exhaust conduit does not extend appreciably into the probe tip. Therefore, the refrigerant exhausting from the supply conduit flows upward along the inside wall of the tip and through the supporting sleeve and flange 18 so that it cools these metallic parts to such a degree that the outside surface of the probe tip and distal end of the shroud become cold enough to freeze tissue. In fact, one can observe on a conventional probe the formation of a frost ring at the junction of the sleeve and probe tip where there is a particularly large mass of metal which is cooled directly by refrigerant. Thus, when the prior probes are inserted into the body, tissue becomes adhered not only to the working end of the tip, but also to proximal portions of the tip and even the distal end of the shroud.

However, by extending the exhaust conduit 34 into tip 22 according to this method so that its end 34a is positioned just proximally of the supply conduit end 32a, the refrigerant from tube 32 is caused to follow a path which sweeps along the inside surface of tip end 22a and leads more or less directly into exhaust tube end 34a as shown by the arrow in FIG. 1. There is little or no refrigerant flow directly through sleeve 16 so that a dead gas space forms in tip 22 above the exhaust conduit end 34a as indicated at D. The stagnant fluid in this space effectively insulates sleeve 16 and the walls of tip 22 proximally of end 34a from flowing refrigerant so that those parts are cooled only be conduction through the probe tip wall. In practice such conduction is insufficient to cool those proximal metallic surfaces to the point where they can freeze tissue.

Thus, the placement of the exhaust conduit end 34a controls the amount of the probe tip 22 that will freeze tissue. That is, if a line L is drawn transversely through the probe tip at the location of conduit end 34a, the portion of the tip distally of line L defined as the freeze zone, will freeze tissue, while the probe parts proximally of line L do not become cold enough to freeze tissue. By properly situating the exhaust tube end 34a inside tip 22, one can adjust the position of line L along the longitudinal axis of the tip 22 and thus control the size of the freeze zone Z. In practice, the conduit end 34a should be situated so that the freeze zone is large enough to form an adequately sized ice ball in the targeted tissue for the particular cryosurgical procedure, but not so large that upper portions of tip 22 unavoidable freeze tissue adjacent to the target area.

Although the inclusion of the exhaust conduit 34 inside tip 22 increases the refrigerant back pressure in the tip on the order of 10%, probe performance is not affected adversely to any significant extent.

The placement of the exhaust conduit end 34ainside probe tip 22 as described also shortens the defrost time or probes having a defrost capability. More particularly, as noted previously, the dead gas space D insulates the metallic parts above the line L from cold refrigerant. Therefore, those parts need not be warmed as much during the defrost cycle of the probe. It follows then that more heat is available to warm the working end of the tip in the frost zone Z and the tissue contacted thereby so that defrost and detachment proceeds more quickly.

Figure 2:
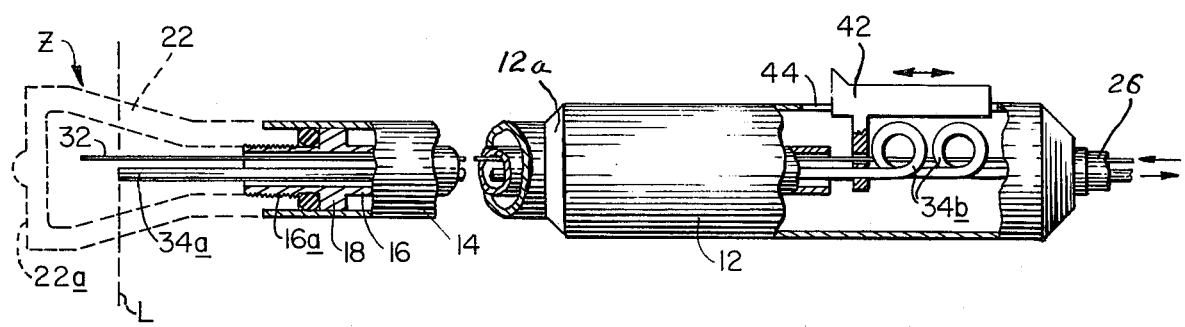
FIG. 2 is a fragmentary perspective view with parts cut away showing a modified version of the probe.

Turning now to FIG. 2, in a modified version of the probe, the exhaust conduit 34 is slidable along the length of the probe so that its end 34a can be positioned at a selected distance proximally of the end of the supply conduit 32. This allows the doctor to adjust the size of the freeze zone Z to suit his needs.

Positioning of the exhaust tube end can be accomplished simply by providing slack in conduit 34, for example, by forming it into loops 34b inside handle 12. Then a slide button 42 is secured to the conduit below loops 34b. The slide button 42 projects through a slot 44 in handle 12 allowing the doctor to adjust the position of conduit end 34a in tip 22 simply by sliding the button 42 along the slot.

Suitable indicia may be provided adjacent the slot to indicate for a given position of button 42 the location of the conduit end 34a and thus the size of the freeze zone Z at the tip.

As noted above, this technique can also be used to control the size of the freeze zone Z at the tip of a probe cooled by liquid refrigerant. This has been done specifically in the case of a probe of the type shown in U.S. Pat. No. 3,7,386. In one embodiment of that probe, a liquid refrigerant is used both to cool the probe tip during the freeze mode of operation and to warm it during the defrost mode of operation. In addition to the usual supply and exhaust conduits leading to the probe tip, that probe has a third small diameter stub conduit exhausting directly to the atmosphere to ensure adequate refrigerant flow during both modes of operation.

To control the size of the freeze zone at the tip of that probe, it exhaust conduit is extended into the probe tip so that it terminates proximally of the end of the supply conduit. In operation, the refrigerant evaporates as it leaves the supply conduit and the fluid flows more or less directly to the exhaust conduit forming a dead gas space in the tip proximally of the end of the exhaust conduit as described above. The third tube is sufficiently small that the flow of refrigerant therethrough does not upset that dead gas space. Accordingly the probe parts proximally of the end of the exhaust conduit are still insulated from refrigerant flow and do not freeze tissue.

It will thus be seen that the objects set forth above among those made apparent from the preceding description are efficiently attained, and since certain changes may be made in carrying out the above steps or in the constructions set forth, it is intended that all matter contained in the above description or shown in the accompanying drawing be interpreted as illustrative and not in a limiting sense.

It is also to be understood that the following claims are intended to cover all of the generic and specific features of the invention herein described.

We claim:

1. A cryosurgical probe comprising
 A. a housing,
 B. a hollow tip protruding from the housing,
 C. means defining an expansion or evaporation chamber in the tip, said means including a surface isolating said chamber from said housing,
 D. a refrigerant supply conduit extending through the housing and through said surface and projecting into said chamber,
 E. a refrigerant exhaust conduit extending through the housing and through said surface and projecting into said chamber, said exhaust conduit terminating inside the chamber short of the supply conduit, and
 F. means for conducting refrigerant to the supply conduit so that the refrigerant exhausts from the end thereof inside the chamber following a path leading more or less directly to the end of the exhaust conduit thereby leaving a region of stagnant gas proximally of the end of the exhaust conduit inside the chamber, said stagnant gas thereby insulating parts of the probe proximally of the end of the exhaust conduit from refrigerant flow so that they do not become cold enough to freeze human tissue.

2. A cryosurgical probe comprising
 A. a housing
 B. a hollow tip protruding from the housing,
 C. means defining an expansion or evaporation chamber in said tip, said means including a surface isolating said chamber from the interior of said housing,
 D. a refrigerant supply conduit extending through the housing and said surface and projecting a selected distance into the chamber,
 E. a refrigerant exhaust conduit extending through the housing and the surface and projecting into said chamber a lesser distance than said selected distance, the end of the exhaust conduit inside the chamber defining the boundary of a freeze zone in the distal end of said chamber so that when refrigerant is flowed through the supply conduit into the chamber the refrigerant does not cool parts of the probe proximally of said boundary to a temperature that is low enough to freeze human tissue, but does cool the chamber, distally of said boundary to a temperature low enough to freeze human tissue.

3. The method of controlling a freeze zone of a cryosurgical probe including a hollow tip having a closed working end comprising the steps of
 A. flowing a refrigerant fluid into the hollow tip of the cryosurgical probe and releasing the fluid into the tip at a point near the closed working end of the tip,
 B. exhausting the refrigerant fluid from the probe tip through an exhaust conduit whose end projects into the tip a lesser distance than the supply conduit so that a stagnant gas space forms in the tip proximally of the end of the exhaust conduit which insulates the parts of the probe proximally of the end of the exhaust conduit from cold refrigerant, and
 C. controlling the size of the freeze zone at the probe tip by adjusting the longitudinal distance between the ends of supply and exhaust conduits inside the probe tip.

4. A cryosurgical probe comprising
 A. a housing,
 B. a hollow tip protruding from the housing,
 C. a refrigerant supply conduit extending through the housing and projecting into the tip,
 D. a refrigerant exhaust conduit extending through the housing and projecting into the tip, said exhaust conduit terminating inside the tip short of the supply conduit,
 E. means for conducting refrigerant to the supply conduit so that the refrigerant exhausts from the end thereof inside the tip following a path leading more or less directly to the end of the exhaust conduit thereby forming a region of stagnant gas proximally of the end of the exhaust conduit inside the tip, said stagnant gas thereby insulating parts of the probe proximally of the end of the exhaust conduit from the refrigerant flow so that they do not become cold enough to freeze human tissue,
 F. means for mounting the exhaust conduit inside the housing so that the end of the exhaust conduit inside the probe tip is slidable longitudinally within the tip, and
 G. means connected to the exhaust conduit and accessible from without the housing for sliding the end of the exhaust conduit inside the tip into position a selected distance short of the end of the supply conduit.

5. A cryosurgical probe comprising
A. a housing,
B. a hollow tip protruding from the housing,
C. a refrigerant supply conduit extending through the housing and projecting a selected distance into the tip,
D. a refrigerant exhaust conduit extending through the housing and projecting into the tip a lesser distance than said selected distance, the end of the exhaust conduit inside the tip defining the boundary of a freeze zone at the tip so that when refigerant is flowed through the supply conduit into the tip the refrigerant does not cool parts of the probe proximally of said boundary to a temperature that is low enough to freeze human tissue, but does cool the working end of the tip distally of said boundary to a temperature low enough to freeze human tissue, and
E. means for adjusting the longitudinal distance between ends of the supply conduit and exhaust conduit inside the probe tip.

* * * * *